(12) United States Patent
Kobayashi et al.

(10) Patent No.: US 12,265,028 B2
(45) Date of Patent: Apr. 1, 2025

(54) OPTICAL MEASUREMENT DEVICE AND WATER QUALITY ANALYSIS SYSTEM

(71) Applicant: HORIBA Advanced Techno, Co., Ltd., Kyoto (JP)

(72) Inventors: Issei Kobayashi, Kyoto (JP); Keigo Sakamoto, Kyoto (JP); Kohei Hara, Kyoto (JP); Kimihiko Arimoto, Kyoto (JP)

(73) Assignee: HORIBA ADVANCED TECHNO, CO., LTD., Kyoto (JP)

( * ) Notice: Subject to any disclaimer, the term of this patent is extended or adjusted under 35 U.S.C. 154(b) by 150 days.

(21) Appl. No.: 17/997,805

(22) PCT Filed: Apr. 13, 2021

(86) PCT No.: PCT/JP2021/015336
§ 371 (c)(1),
(2) Date: Nov. 2, 2022

(87) PCT Pub. No.: WO2021/229980
PCT Pub. Date: Nov. 18, 2021

(65) Prior Publication Data
US 2023/0288332 A1    Sep. 14, 2023

(30) Foreign Application Priority Data

May 15, 2020 (JP) ................. 2020-086213

(51) Int. Cl.
*G01N 21/53* (2006.01)
*G01N 21/51* (2006.01)
*G01N 33/18* (2006.01)

(52) U.S. Cl.
CPC .......... *G01N 21/532* (2013.01); *G01N 21/51* (2013.01); *G01N 33/1893* (2013.01); *G01N 2201/0636* (2013.01)

(58) Field of Classification Search
CPC ...... G01N 21/532; G01N 21/51; G01N 21/03; G01N 21/05; G01N 2021/513;
(Continued)

(56) References Cited

U.S. PATENT DOCUMENTS 3,880,526 A    4/1975  Kobayashi et al.
4,345,837 A *  8/1982  Kallet .................... G01N 21/64
                                                    356/244
(Continued)

FOREIGN PATENT DOCUMENTS

CN    103597525 A    2/2014
CN    105203505 A    12/2015
(Continued)

OTHER PUBLICATIONS

Cao P, Zhu Y, Zhao W, Liu S, Gao H. Chromaticity Measurement Based on the Image Method and Its Application in Water Quality Detection. Water. 2019; 11(11):2339. https://doi.org/10.3390/w11112339 (Year: 2019).*

(Continued)

*Primary Examiner* — Tarifur R Chowdhury
*Assistant Examiner* — Jonathon Cook
(74) *Attorney, Agent, or Firm* — Alleman Hall & Tuttle LLP

(57) ABSTRACT

To accurately measure chromaticity and turbidity while achieving downsizing and employing a turbidity measurement method based on water quality standards of each country, an optical measurement includes a cell that accommodates a liquid sample, a transmitted light measurement light source that irradiates the liquid sample in the cell with light for transmittance, a scattered light measurement light source that irradiates the liquid sample in the cell with light for scattering, a photodetector that detects light from both sources, and a reflection mirror that reflects the light for (Continued)

transmittance in the cell to cause the light for transmittance to be directed to the photodetector. The scattered light measurement light source emits the light for scattering toward a post-reflection optical path of the light for transmittance reflected by the reflection mirror and directed to the photodetector so that the light for scattering intersects the post-reflection optical path at a predetermined angle.

9 Claims, 3 Drawing Sheets

(58) Field of Classification Search
 CPC ..... G01N 2021/473; G01N 2201/0636; G01N 33/1893; G01J 3/46; G01J 3/50
 See application file for complete search history.

(56) References Cited

U.S. PATENT DOCUMENTS

| | | | | |
|---|---|---|---|---|
| 6,795,177 | B2* | 9/2004 | Doyle | G01J 3/44 356/301 |
| 7,262,844 | B2* | 8/2007 | Larsen | G01N 21/31 356/416 |
| 9,013,700 | B2* | 4/2015 | Aldstadt, III | G01J 3/0291 356/436 |
| 9,518,866 | B2* | 12/2016 | Feitisch | G01J 3/0291 |
| 2007/0046942 | A1* | 3/2007 | Ng | G01N 21/251 356/442 |
| 2007/0077178 | A1 | 4/2007 | Wagner | |
| 2011/0080583 | A1 | 4/2011 | Rabus et al. | |
| 2013/0271756 | A1* | 10/2013 | Bojarski | G01J 3/14 356/300 |
| 2015/0146204 | A1 | 5/2015 | Shibuya et al. | |
| 2018/0246035 | A1* | 8/2018 | Hasegawa | G01N 33/18 |
| 2021/0063981 | A1* | 3/2021 | Kitagawa | C02F 1/00 |

FOREIGN PATENT DOCUMENTS

| | | | |
|---|---|---|---|
| JP | 2008232790 A | * | 10/2008 |
| JP | 2011513717 A | | 4/2011 |
| JP | 2013050335 A | | 3/2013 |
| JP | 2015031525 A | | 2/2015 |
| WO | 2012127650 A | | 9/2012 |

OTHER PUBLICATIONS

ISA Japan Patent Office, International Search Report Issued in Application No. PCT/JP2021/015336, Jun. 29, 2021, WIPO, 4 pages.

European Patent Office, Office Action Issued in Application No. 21804026.9, Apr. 15, 2024, Germany, 5 pages.

China National Intellectual Property Administration, Office Action and Search Report Issued in Application No. 202180033072.4, Nov. 8, 2024, 20 pages.

* cited by examiner

OPTICAL MEASUREMENT DEVICE AND WATER QUALITY ANALYSIS SYSTEM

TECHNICAL FIELD

The present invention relates to an optical measurement device for measuring chromaticity and turbidity of a liquid sample and a water quality analysis system including the optical measurement device.

BACKGROUND ART

As an optical measurement device (hereinafter, a chromaticity and turbidity measurement device) for measuring chromaticity and turbidity, as disclosed in Patent Literature 1, a device for measuring chromaticity and turbidity by detecting transmitted light transmitted through a liquid sample is known.

In a case where this chromaticity and turbidity measurement device is used, for example, for water quality management of purified water supplied as tap water or wastewater from a factory, it may be required to simultaneously measure not only chromaticity and turbidity but also other water quality indexes such as residual chlorine, pH, and conductivity from the viewpoint of water quality regulation.

For this reason, it is required to downsize a chromaticity and turbidity measurement device in order to facilitate use of the chromaticity and turbidity measurement device together with a plurality of optical measurement devices that measure other water quality indexes. Here, in order to downsize a chromaticity and turbidity measurement device, it is conceivable to reduce size of a cell that accommodates a liquid sample.

However, if the cell is made small, an optical path length between a light source and a photodetector becomes short. Then, there is a problem that a change in transmitted light intensity with respect to a fluctuation in chromaticity and turbidity becomes small, resolution deteriorates, and measurement accuracy deteriorates.

Further, in order to conform to water quality standards of each country, it may be required to measure turbidity with scattered light at a predetermined angle, and the above chromaticity and turbidity measurement device cannot perform measurement conforming to the water quality standards.

CITATION LIST

Patent Literature

Patent Literature 1: JP 2013-50335 A

SUMMARY OF INVENTION

Technical Problem

The present invention has been made in view of the above-described problem, and it is a main object of the present invention to accurately measure chromaticity and turbidity while achieving downsizing and employing a turbidity measurement method based on water quality standards of each country.

Solution to Problem

That is, an optical measurement device according to the present invention is an optical measurement device for measuring turbidity of a liquid sample by measuring scattered light scattered by the liquid sample. The optical measurement device includes a cell that accommodates the liquid sample, a transmitted light measurement light source that irradiates the liquid sample in the cell with light for measuring transmitted light, a scattered light measurement light source that irradiates the liquid sample in the cell with light for measuring scattered light, a photodetector that detects transmitted light of the light for measuring transmitted light and scattered light of the light for measuring scattered light, and a reflection mirror that is provided in the cell and reflects the light for measuring transmitted light in the cell to cause the light for measuring transmitted light to be directed to the photodetector. The scattered light measurement light source emits the light for measuring scattered light toward a post-reflection optical path that is an optical path of the light for transmitted light reflected by the reflection mirror and directed to the photodetector so that the light for measuring scattered light intersects the post-reflection optical path at a predetermined angle.

With such an optical measurement device, the light for measuring transmitted light emitted from the light source for measuring transmitted light is reflected by the reflection mirror and directed to the photodetector, so that, even in a case where the cell is downsized, an optical path length of the light for measuring transmitted light in the cell can be secured. As a result, for example, chromaticity or turbidity of purified water such as tap water can also be accurately measured by transmitted light measurement.

Further, since the scattered light measurement light source emits the light for measuring scattered light toward the post-reflection optical path of the light for measuring transmitted light such that the light for measuring scattered light intersects the post-reflection optical path at a predetermined angle, the photodetector detects scattered light at a predetermined angle of the light for measuring scattered light. Here, since the light for measuring scattered light is emitted toward the post-reflection optical path, a distance between a turbidity measurement point and the photodetector can be shortened. As a result, scattered light at a predetermined angle scattered by the liquid sample can be detected by the photodetector before being attenuated, and turbidity of the liquid sample can be accurately measured.

In order to further downsize the entire optical measurement device, the transmitted light measurement light source, the scattered light measurement light source, and the photodetector are desirably provided in the cell.

In order to generate scattered light of a predetermined angle while shortening an optical path length between a turbidity measurement point in the post-reflection optical path of the light for measuring transmitted light and the scattered light measurement light source and suppressing attenuation of the light for measuring scattered light, the scattered light measurement light source is desirably provided on the post-reflection optical path side in the cell.

In a case where the turbidity measurement light source and the photodetector are provided in the cell, there is a possibility that direct light from the scattered light measurement light source is detected by the photodetector in an internal space of the cell, and measurement accuracy is deteriorated.

In order to suitably solve this problem and improve accuracy of turbidity measurement, a protruding portion is desirably formed between the scattered light intensity measurement light source and the photodetector on an inner surface of the cell, the protruding portion suppressing direct incidence of the light for measuring turbidity light emitted from the scattered light measurement light source on the photodetector.

In a case of the cell into which the liquid sample is introduced, air bubbles may accumulate in the cell to deteriorate measurement accuracy. In order to prevent deterioration in measurement accuracy due to the air bubbles, a configuration in which an introduction port for introducing the liquid sample is formed in a lower end portion of the cell, and an outlet port for discharging the liquid sample is formed in an upper end portion of the cell is desirably employed.

Even in a case where this configuration is employed, air bubbles are attached to or accumulate in the outlet port or the vicinity of the outlet port, and scattered light due to the air bubbles becomes a factor of a measurement error. For this reason, in the optical measurement device of the present invention, the scattered light measurement light source and the photodetector are desirably arranged so as to sandwich the outlet port, and the protruding portion is desirably formed between the outlet port and the scattered light measurement light source. With this configuration, even in a case where air bubbles are attached to or accumulate in the outlet port or the vicinity of the outlet port, it is possible to suppress scattering of the light for measuring scattered light by the air bubbles and to prevent deterioration in accuracy of turbidity measurement.

Further, in an optical analysis device of the present invention, a surface of an inner surface of the cell facing the scattered light measurement light source is desirably configured not to reflect the light for measuring scattered light toward the photodetector.

With this configuration, it is possible to prevent light other than scattered light at a predetermined angle in the light for measuring scattered light from being detected by the photodetector and to improve accuracy of turbidity measurement.

Advantageous Effects of Invention

According to the present invention, it is possible to accurately measure turbidity and chromaticity while achieving downsizing and employing a turbidity measurement method based on water quality standards in each country.

LIST OF REFERENCE CHARACTERS

Figure 1:
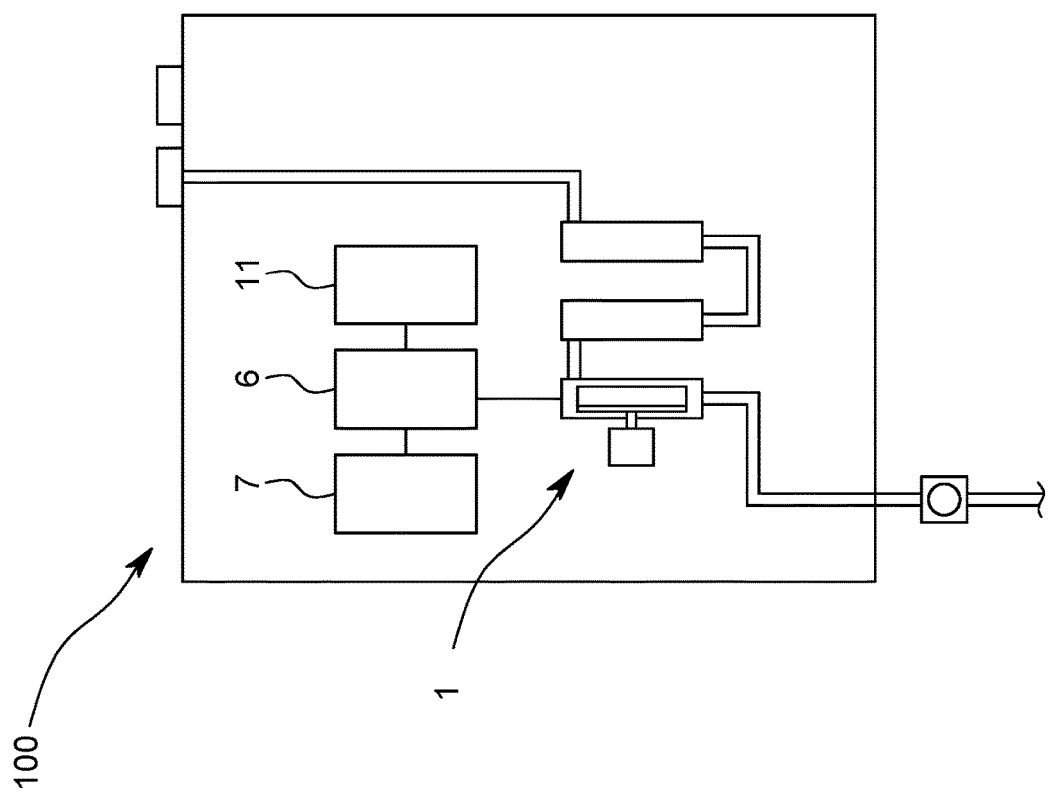
FIG. 1 is a schematic diagram illustrating a water quality analysis system according to an embodiment of the present invention.

100 water quality analysis system
1 chromaticity and turbidity measurement device
2 cell
P1 introduction port
P2 outlet port
2T protruding portion
3 chromaticity measurement light source
4 turbidity measurement light source
5 photodetector
8 reflection mirror

DESCRIPTION OF EMBODIMENT

Hereinafter, an embodiment of the present invention will be described with reference to the drawings.

An optical measurement device 1 according to the present embodiment is a chromaticity and turbidity measurement device 1 that optically measures chromaticity and turbidity of a liquid sample. As illustrated in FIG. 1, for example, the chromaticity and turbidity measurement device 1 is provided in a water supply pipe distal passage or the like that distributes water purified in a water purification plant to each house, and is used by being incorporated in a water quality analysis system 100 that monitors a change in water quality of water flowing through a waterworks.

In addition to the chromaticity and turbidity measurement device 1, the water quality analysis system 100 may include, for example, a residual chlorine concentration measurement device that measures residual chlorine concentration of a liquid sample, a conductivity measurement device that measures conductivity of a liquid sample, a pH measurement device that measures pH of a liquid sample, a pressure sensor, a temperature sensor, or the like.

The chromaticity and turbidity measurement device 1 includes a chromaticity measurement optical system for measuring chromaticity and a turbidity measurement optical system for measuring turbidity.

Specifically, the chromaticity and turbidity measurement device 1 includes a cell 2 that accommodates a liquid sample, a transmitted light measurement light source 3 (hereinafter, also referred to as chromaticity measurement light source 3) that irradiates a liquid sample accommodated in the cell 2 with light for measuring transmitted light (hereinafter, also referred to as light for measuring chromaticity), a scattered light measurement light source 4 (hereinafter, also referred to as turbidity measurement light source 4) that irradiates a liquid sample accommodated in the cell 2 with light for measuring scattered light (hereinafter, also referred to as light for measuring turbidity), and a photodetector 5 that detects transmitted light L1 emitted from the chromaticity measurement light source 3 and transmitted through a liquid sample and scattered light L2 emitted from the turbidity measurement light source 4 and scattered by a liquid sample. A light intensity signal, which is output from the photodetector 5, is output to a calculation unit 6, and the calculation unit 6 calculates chromaticity and turbidity of a liquid sample. Chromaticity and turbidity calculated by the calculation unit 6 are displayed on a display unit 7. A control unit 11 that controls operation of these constituent elements may be further included. Note that the calculation unit 6 and/or the control unit 11 is configured using, for example, a computer including a CPU, a memory, an input and output interface, an AD converter, and the like.

The cell 2 has a storage space 2S for storing a liquid sample in the inside, and includes an introduction port P1 for introducing a liquid sample into the storage space 2S and an outlet port P2 for discharging a liquid sample from the storage space 2S to the outside.

Figure 2:
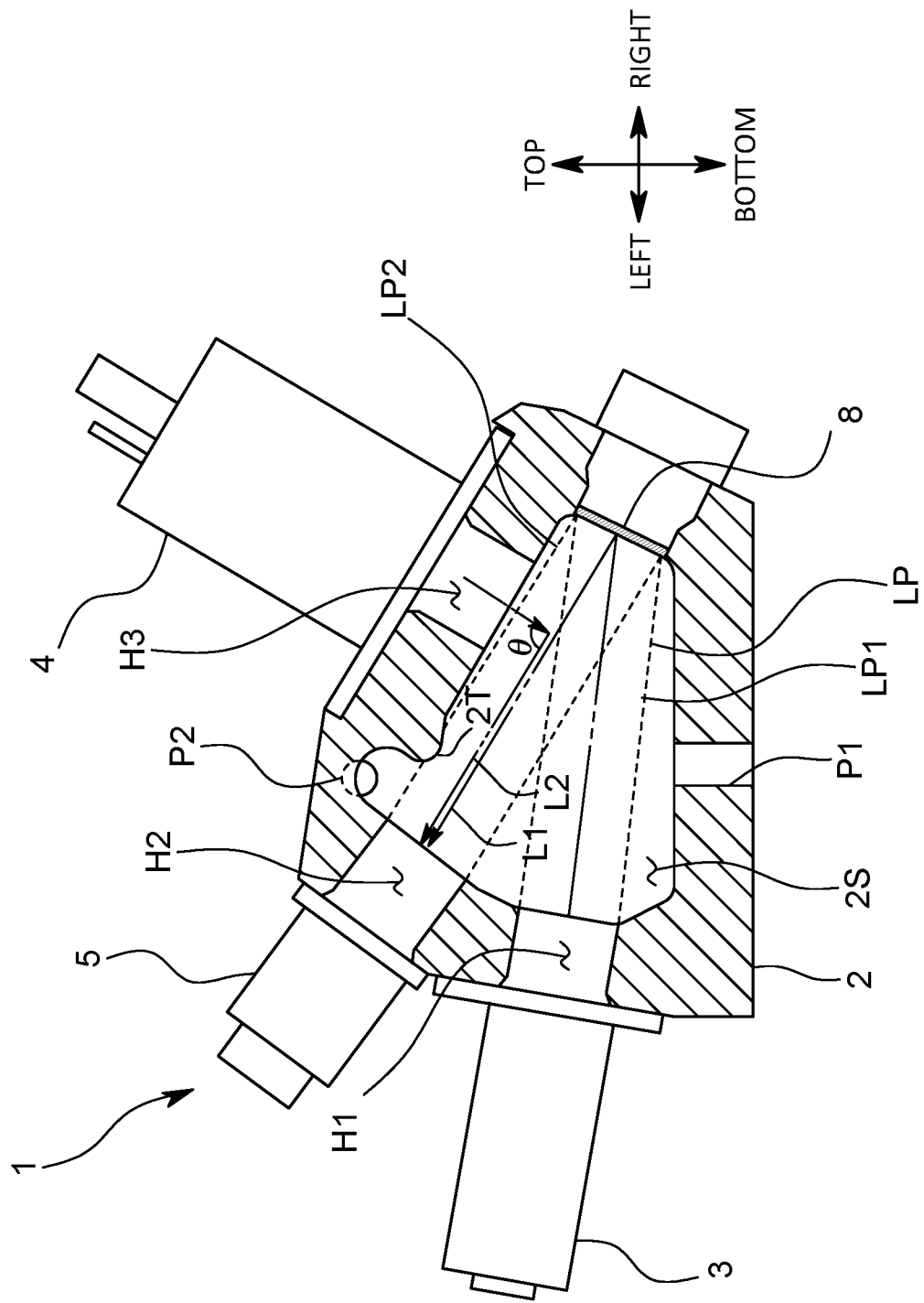
FIG. 2 is a schematic plan view of a chromaticity and turbidity measurement device according to the present embodiment.

Specifically, as illustrated in FIG. 2, the cell 2 has, for example, a flat external appearance shape in which the storage space 2S having a substantially flat plate shape is formed. Then, the introduction port P1 is formed in a lower end portion of the cell 2, and introduces a liquid sample from the lower end of the storage space 2S. Further, the outlet port P2 is formed in an upper end portion of the cell 2, and discharges a liquid sample from the upper end of the storage space 2S. Note that the introduction port P1 opens upward in a center portion at the lower end of the cell 2, and the outlet port P2 opens to the side immediately above the introduction port P1. However, the present invention is not limited to this.

Further, an upper surface of the cell 2 in a portion where the outlet port P2 is formed is gradually cut upward toward an outlet of the outlet port P2.

The chromaticity measurement light source 3 is provided in the cell 2 and emits light (light for measuring chromaticity) in a wavelength band that is easily absorbed by a liquid sample accommodated in the cell 2. The chromaticity measurement light source 3 emits light in a wavelength band of 200 nm or more and 400 nm or less, for example. In the present embodiment, as an example, an LED that emits light having a wavelength of 375 nm is used.

The turbidity measurement light source 4 is provided in the cell 2 and emits light (light for measuring turbidity) in a wavelength band that is easily scattered by a liquid sample accommodated in the cell 2. The turbidity measurement light source 4 emits light having a wavelength of, for example, 600 nm or more and 900 nm or less, more preferably 830 nm or more and 890 nm or less. In the present embodiment, as an example, an LED that emits light having a wavelength of 870 nm is used.

The photodetector 5 is provided in the cell 2, constitutes a chromaticity measurement optical system together with the chromaticity measurement light source 3, and constitutes a turbidity measurement optical system together with the turbidity measurement light source 4. Specifically, as illustrated in FIG. 2, the photodetector 5 detects the transmitted light L1 emitted from the chromaticity measurement light source 3 and transmitted through a liquid sample in the storage space 2S, and detects the scattered light L2 emitted from the turbidity measurement light source 4 and scattered by a liquid sample in the storage space 2S. In the present embodiment, since the chromaticity measurement light source 3 and the turbidity measurement light source 4 are alternately turned on, the photodetector 5 alternately detects the transmitted light L1 of the light for measuring chromaticity and the scattered light L2 of the light for measuring turbidity. The photodetector 5 can be configured using, for example, a photodiode.

Thus, the chromaticity and turbidity measurement device 1 according to the present embodiment further includes, as a chromaticity measurement optical system, a reflection mirror 8 that is provided in the cell 2, reflects light emitted from the chromaticity measurement light source 3, and guides the light to the photodetector 5.

Next, optical arrangement of the chromaticity measurement light source 3, the turbidity measurement light source 4, the photodetector 5, and the reflection mirror 8 in the cell 2 and a structure of the cell 2 for the optical arrangement will be described.

The chromaticity measurement light source 3 and the photodetector 5 are provided on the same side (left side in FIG. 2) in the cell 2. Specifically, the chromaticity measurement light source 3 and the photodetector 5 are provided on a left wall portion of the cell 2, the chromaticity measurement light source 3 is arranged to emit the light for measuring chromaticity along a longitudinal direction of the storage space 2S, and the photodetector 5 is arranged above the chromaticity measurement light source 3. Note that, in the cell 2, an introduction hole H1 for introducing the light for measuring chromaticity from the chromaticity measurement light source 3 into the storage space 2S is formed, and a detection hole H2 for the photodetector 5 to detect the transmitted light L1 of the light for measuring chromaticity and the scattered light L2 of the light for measuring turbidity is formed.

Further, the reflection mirror 8 is provided on the opposite side (right side in FIG. 2) to the chromaticity measurement light source 3 so as to face the chromaticity measurement light source 3 in the cell 2. Specifically, the reflection mirror 8 is provided on a right wall portion of the cell 2 and is provided so as to be exposed to an inner surface of the storage space 2S. Here, the reflection mirror 8 is arranged at an angle at which the light for measuring chromaticity is directed to the photodetector 5, and the light for measuring chromaticity reflected by the reflection mirror 8 is detected by the photodetector 5 after passing along a longitudinal direction of the storage space 2S.

With the above arrangement, in the chromaticity measurement optical system, as illustrated in FIG. 2, a chromaticity measurement optical path LP is formed between the chromaticity measurement light source 3 and the photodetector 5. The chromaticity measurement optical path LP includes an optical path LP1 (pre-reflection optical path LP1) before reflection from the chromaticity measurement light source 3 to the reflection mirror 8 and an optical path LP2 (post-reflection optical path LP2) after reflection from the reflection mirror 8 to the photodetector 5.

On the other hand, the turbidity measurement light source 4 is arranged to emit the light for measuring turbidity toward the post-reflection optical path LP2 of the light for measuring chromaticity so that the light intersects the post-reflection optical path LP2 at a predetermined angle (θ). In the present embodiment, θ is 90 degrees. Specifically, the turbidity measurement light source 4 is arranged on the post-reflection optical path LP2 side in the cell 2. Here, the turbidity measurement light source 4 emits light along a plane formed by the pre-reflection optical path LP1 and the post-reflection optical path LP2. More specifically, the turbidity measurement light source 4 is provided on an upper wall portion of the cell 2. Note that an introduction hole H3 for introducing the light for measuring turbidity from the turbidity measurement light source 4 into the storage space 2S is formed on an upper wall portion of the cell 2.

By arranging the turbidity measurement light source 4, a detection axis of the photodetector 5 and an optical axis of the turbidity measurement light source 4 intersect (orthogonally intersect) at a predetermined angle (θ). Further, an optical axis of the scattered light L2 at 90 degrees of the light for measuring turbidity coincides with a detection axis (post-reflection optical path LP2) of the photodetector 5.

Further, in the above arrangement, the turbidity measurement light source 4 and the photodetector 5 are arranged so as to sandwich the outlet port P2. Here, in order to prevent light from the turbidity measurement light source 4 from being directly detected by the photodetector 5, a protruding portion 2T is formed between the outlet port P2 and the turbidity measurement light source 4. The protruding portion 2T is formed as an inner surface forming the storage space 2S protrudes inward. The protruding portion 2T of the present embodiment is provided so as to protrude downward from an upper surface of the storage space 2S, and is entirely formed of a curved surface.

Further, in an inner surface of the storage space 2S, a surface facing a surface to which the turbidity measurement light source 4 is attached is configured not to reflect light emitted from the turbidity measurement light source 4 toward the photodetector 5. In the present embodiment, the surface facing the surface to which the turbidity measurement light source 4 is attached corresponds to a bottom surface of the storage space 2S. In view of the above, in the present embodiment, the bottom surface has an angle and a shape by which light from the turbidity measurement light source 4 is not reflected toward the photodetector 5. Further, in the present embodiment, an incident angle of light from the turbidity measurement light source with respect to the bottom surface is set to a predetermined angle such that the light reflected by the bottom surface formed as described above is directed toward the chromaticity measurement light source or the turbidity measurement light source.

The chromaticity and turbidity measurement device 1 according to the present embodiment may further include a removal mechanism 9 that removes an attached substance and the like to the introduction holes (H1 and H3), a window separating the detection hole H2 and the inside of the storage space 2S, and a surface of the reflection mirror 8 in contact with a liquid sample in the storage space 2S.

Figure 3:
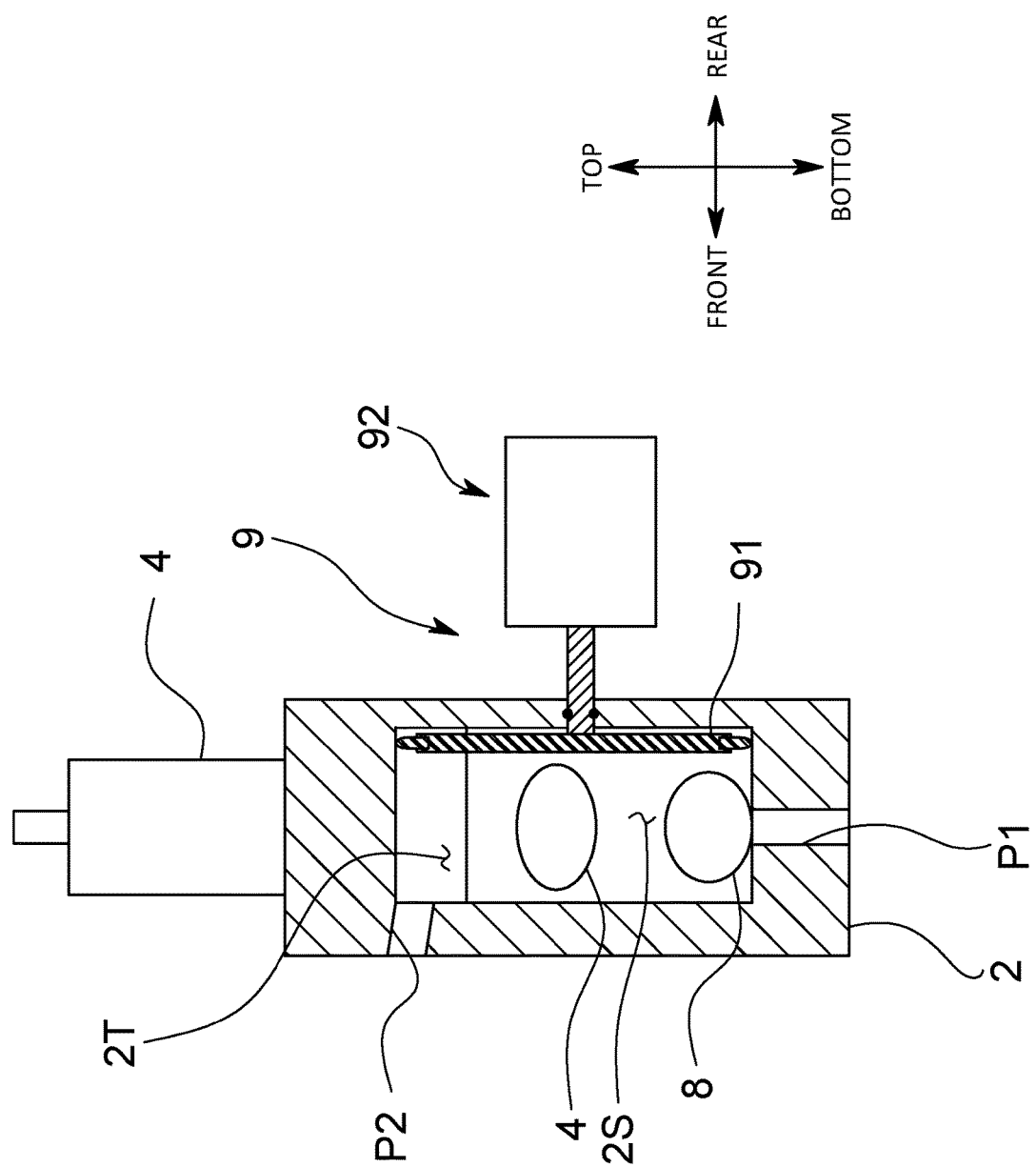
FIG. 3 is a schematic cross-sectional view of the chromaticity and turbidity measurement device according to the present embodiment as viewed from the side.

For example, as illustrated in FIG. 3, the removal mechanism 9 includes a wiper 91 and a drive unit 92 that drives the wiper 91.

The wiper 91 includes, for example, an elastic member that comes into contact with the introduction holes (H1 and H3), the window that separates the detection hole H2 and the inside of the storage space 2S, and the surface of the reflection mirror 8 on a sample solution side and wipes them.

The wiper 91 has, for example, a shape conforming to an internal shape of the storage space 2S, and is arranged on one end side of the storage space 2S as illustrated in FIG. 3, and is configured to move to the other end along an inner surface of the storage space 2S, in a front-rear direction in FIG. 3, by power transmitted from the drive unit 92 between measurements or the like.

According to the chromaticity and turbidity measurement device 1 configured as described above, since a mirror that reflects light from a light source in the cell 2 and guides the light to the photodetector 5 is provided, a transmission distance of the transmitted light L1 inside the cell 2 can be sufficiently secured even in a case where the cell 2 is downsized. As a result, for example, chromaticity of purified water such as tap water can also be accurately measured.

The turbidity measurement light source 4 is arranged on the post-reflection optical path LP2 side so as to be adjacent to the photodetector 5, and performs emission toward the post-reflection optical path LP2 of the light for measuring chromaticity in a manner orthogonal to the post-reflection optical path LP2. For this reason, in a case where the scattered light L2 at 90 degrees of the light for measuring turbidity is detected by the photodetector 5, a distance from the turbidity measurement light source 4 to a turbidity measurement point on the post-reflection optical path LP2 and a distance from the turbidity measurement point to the photodetector 5 can be shortened. As a result, it is possible to suppress attenuation of the light for measuring turbidity before reaching the turbidity measurement point. Further, light scattered by a liquid sample at the turbidity measurement point can be captured by the photodetector 5 before being attenuated. Furthermore, since light scattered at the turbidity measurement point enters the photodetector 5 before spreading in directions, more light can be detected by the photodetector 5.

As a result, turbidity of a liquid sample can be accurately measured.

Since the outlet port P2 is formed at the upper end of the storage space 2S, and an upper surface of the cell 2 in a portion where the outlet port P2 is formed is gradually cut upward toward the outlet of the outlet port P2, even if a liquid sample contains a bubble, the bubble is easily discharged to the outside of the storage space 2S.

Since the chromaticity measurement light source 3 emits light along a longitudinal direction of the storage space 2S, and the reflection mirror 8 reflects the light from the chromaticity measurement light source 3 along the longitudinal direction and guides the light to the photodetector 5, the optical path LP for chromaticity measurement can be made as long as possible.

Since the chromaticity measurement light source 3, the photodetector 5, and the turbidity measurement light source 4 are all provided in the cell 2, it is possible to save time and effort to adjust a positional relationship of the chromaticity measurement light source 3, the photodetector 5, and the turbidity measurement light source 4 with respect to the cell 2. Further, for example, it is possible to simplify attaching work in a case where the chromaticity and turbidity measurement device 1 is attached to a water quality analysis system.

Since the chromaticity measurement light source 3, the photodetector 5, and the turbidity measurement light source 4 can be arranged side by side on the same plane, it is easy to use them side by side with another measurement device while saving unnecessary space as much as possible.

Since the protruding portion 2T is formed between the turbidity measurement light source 4 and the photodetector 5, light emitted from the turbidity measurement light source 4 is prevented from directly entering the photodetector 5, and accuracy of turbidity measurement can be improved.

Since the protruding portion 2T is provided between the outlet port P2 and the turbidity measurement light source 4, even if air bubbles are accumulated in the outlet port P2, it is possible to prevent light from the turbidity measurement light source 4 from hitting and scattering the air bubbles, and to further reduce noise for chromaticity measurement and turbidity measurement.

Since the protruding portion 2T is entirely formed of a curved surface, it is possible to suppress formation of a corner and to suppress noise in chromaticity measurement and turbidity measurement due to reflection of light at a corner portion.

Since the bottom surface of the storage space 2S, which is a surface facing the turbidity measurement light source 4, has an angle and a shape by which light emitted from the turbidity measurement light source 4 is not reflected toward the photodetector 5, and an incident angle of light from the turbidity measurement light source with respect to the bottom surface is set to a predetermined angle such that light reflected by the bottom surface is directed toward the chromaticity measurement light source or the turbidity measurement light source, it is possible to prevent light from the turbidity measurement light source 4 reflected by the bottom surface from being detected by the photodetector 5 and to suppress an adverse effect on the turbidity measurement.

Since the removal mechanism 9 for removing dirt on the introduction holes (H1 and H3), the window separating the detection hole H2 and the inside of the storage space 2S, and a surface of the reflection mirror 8 in contact with a liquid sample in 2S the storage space 2S is provided, it is possible to suppress an error in chromaticity measurement and turbidity measurement due to attachment of dirt to surfaces of the window and the reflection mirror 8 without cleaning the window and the reflection mirror 8 by disassembling the cell.

Since the wiper 91 has a shape conforming to an internal shape of the storage space 2S, dirt on the window and the surface of the reflection mirror 8 in contact with a liquid sample in the storage space 2S can be removed with a configuration as simple as possible. Since only one of the wiper 91 is provided, the entire optical measurement device can be downsized as compared with a case where a plurality of the wipers 91 are provided.

The present invention is not limited to the above-described embodiment.

For example, when a condenser lens is provided between the turbidity measurement light source and the storage space, light emitted from the turbidity measurement light source can be condensed on the post-reflection optical path LP2. As a result, it is possible to prevent light from the turbidity measurement light source from being directly detected by the photodetector, similarly to the case where there is the protruding portion, without providing the protruding portion. As a result, it is possible to improve measurement accuracy of turbidity without forming the protruding portion.

In the above embodiment, the photodetector is provided above the chromaticity measurement light source, but the chromaticity measurement light source may be arranged above the photodetector, or the photodetector may be arranged on the side of the chromaticity measurement light source depending on a shape of the cell or the storage space.

Further, a position of the reflection mirror may be any position as long as light from the chromaticity measurement light source can be reflected toward the photodetector, and may be appropriately changed in accordance with them.

Arrangement of the turbidity measurement light source may also be appropriately changed as long as the turbidity measurement light source is on the post-reflection optical path side and at a position where light perpendicular to the post-reflection optical path LP2 can be emitted.

The turbidity measurement light source is preferably arranged on the post-reflection light path side because a distance between the turbidity measurement light source and the photodetector can be further shortened, but it is sufficiently possible to measure turbidity even if the turbidity measurement light source is arranged on the pre-reflection light path side.

The chromaticity measurement light source, the turbidity measurement light source, and the photodetector are not necessarily provided in the cell, and may be arranged separately from the cell.

In the above embodiment, one that measures chromaticity of a liquid sample by measuring transmitted light transmitted through the liquid sample is described. However, the present invention is not limited to this. For example, when a wavelength of the transmitted light measurement light source is changed, turbidity of a liquid sample can be measured as transmitted light is measured.

In the embodiment described above, one in which the scattered light turbidity measurement light source is of a 90 degree scattering type that emits the light for measuring scattered light turbidity such that the light is orthogonal to the post-reflection optical path is described. However, this angle may be, for example, 60 degrees, 120 degrees, 150 degrees, or the like by employing the predetermined angle θ determined based on water quality standards of each country.

The water quality analysis system is not limited to one arranged in a water supply pipe distal passage, and may be, for example, one arranged at a terminal of a water purification plant, or may be provided in a flow path or the like before or during purification in a water purification plant. The water quality analysis system may be used for water quality monitoring for various types of water, such as river water, seawater, and factory wastewater.

The chromaticity and turbidity measurement device does not necessarily need to be used in combination with another measurement device, and can be used alone.

Various modifications and combinations of embodiments may be made without departing from the spirit of the present invention.

INDUSTRIAL APPLICABILITY

According to the present invention, it is possible to accurately measure chromaticity and turbidity while achieving downsizing and employing a turbidity measurement method based on water quality standards in each country.

The invention claimed is:

1. An optical measurement device for measuring turbidity of a liquid sample by measuring scattered light scattered by the liquid sample, the optical measurement device comprising:
a cell that accommodates the liquid sample;
a transmitted light measurement light source that irradiates the liquid sample in the cell with light for measuring transmitted light;
a scattered light measurement light source that irradiates the liquid sample in the cell with light for measuring scattered light;
a photodetector that detects transmitted light of the light for measuring transmitted light and scattered light of the light for measuring scattered light; and
a reflection mirror that is provided in the cell and reflects the light for measuring transmitted light in the cell to cause the light for measuring transmitted light to be directed to the photodetector,
wherein the scattered light measurement light source emits the light for measuring scattered light toward a post-reflection optical path that is an optical path of the light for transmitted light reflected by the reflection mirror and directed to the photodetector so that the light for measuring scattered light intersects the post-reflection optical path at a predetermined angle, and
wherein a surface of an inner surface of the cell facing the scattered light measurement light source is shaped to not reflect the light for measuring scattered light toward the photodetector.

2. The optical measurement device according to claim 1, wherein the predetermined angle is 90 degrees or 60 degrees.

3. The optical measurement device according to claim 1, wherein chromaticity of the liquid sample is measured by measurement of the transmitted light.

4. The optical measurement device according to claim 1, wherein the transmitted light measurement light source, the scattered light measurement light source, and the photodetector are provided in the cell.

5. The optical measurement device according to claim 4, wherein the scattered light measurement light source is provided on the reflected light path side in the cell.

6. The optical measurement device according to claim 1, wherein a protruding portion is formed between the scattered light measurement light source and the photodetector on the inner surface of the cell, the protruding portion suppressing direct incidence of the light for measuring scattered light emitted from the scattered light measurement light source on the photodetector.

7. The optical measurement device according to claim 6, wherein an introduction port through which the liquid sample is introduced is formed in a lower end portion of the cell, and an outlet port through which the liquid sample is discharged is formed in an upper end portion of the cell, the scattered light measurement light source and the photodetector are arranged so as to sandwich the outlet port, and the protruding portion is formed between the outlet port and the scattered light measurement light source.

8. The optical measurement device according to claim 1, further comprising a condenser lens that condenses the light for measuring scattered light emitted from the scattered light measurement light source on the post-reflection optical path.

9. A water quality analysis system comprising the optical measurement device according to claim 1.

* * * * *